(12) United States Patent
Eliav

(10) Patent No.: US 7,827,644 B2
(45) Date of Patent: *Nov. 9, 2010

(54) TOOTHBRUSH WITH RESILIENT HEAD SECTION

(75) Inventor: Eyal Eliav, New York, NY (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/200,299

(22) Filed: Aug. 28, 2008

(65) Prior Publication Data

US 2009/0007350 A1 Jan. 8, 2009

Related U.S. Application Data

(62) Division of application No. 10/260,620, filed on Sep. 27, 2002, now Pat. No. 7,430,776.

(51) Int. Cl.
*A61C 17/22* (2006.01)
*A61C 17/34* (2006.01)

(52) U.S. Cl. ............................................ 15/22.1; 15/28
(58) Field of Classification Search ................. 15/22.1, 15/22.2, 28
See application file for complete search history.

(56) References Cited

U.S. PATENT DOCUMENTS 5,524,312 A 6/1996 Tan et al.
5,617,603 A 4/1997 Mei
5,732,433 A 3/1998 Goecking et al.
5,836,030 A 11/1998 Hazeu
6,938,293 B2 9/2005 Eliav et al.
6,938,294 B2 9/2005 Fattori et al.
2001/0020314 A1 9/2001 Calabrese
2003/0126698 A1 7/2003 Fritsch et al.

FOREIGN PATENT DOCUMENTS

WO 0132095 5/2001
WO 0205725 1/2002

*Primary Examiner*—Randall Chin
(74) *Attorney, Agent, or Firm*—Amy M. Fernandez

(57) ABSTRACT

A powered toothbrush is provided and includes a handle portion having a neck formed at one end and a head coupled to the neck. The head includes a first carrier coupled to the head and operatively connected to a drive mechanism for moving the first carrier in a first path of motion. The first carrier has at least one of a plurality of bristles and elastomeric cleaning members extending outwardly therefrom to deliver oral care benefits to the user. The head also includes a second carrier coupled to the head. The second carrier is formed of an elastomeric material and has at least one of a plurality of bristles and elastomeric cleaning members extending outwardly from an upper surface thereof. The second carrier is constructed so that upon application of a force to the upper surface thereof, the second carrier moves in a second path of motion that is different from the first path of motion.

20 Claims, 7 Drawing Sheets

TOOTHBRUSH WITH RESILIENT HEAD SECTION

CROSS-REFERENCE TO RELATED APPLICATIONS

The present application is a divisional of U.S. patent application Ser. No. 10/260,620 filed on Sep. 27, 2002 and which has been allowed as U.S. Pat. No. 7,430,776, the entirety of which is hereby incorporated by reference.

BACKGROUND OF THE INVENTION

1. Field of the Invention

The present invention relates to powered toothbrushes, and more particularly, to a toothbrush having a head with two distinct moving sections with each section providing oral health benefits to the user.

2. Discussion of Related Art

Toothbrushes provide many oral hygiene benefits. For example, toothbrushes remove plaque and food debris to help avoid tooth decay and disease. They remove stained pellicle from the surface of each tooth to help whiten the teeth. Also, the bristles combined with the brushing motion massage the gingival tissue for stimulation and increased health of the tissue.

Powered toothbrushes have been available for some time. Powered toothbrushes have advantages over manual (non-powered) toothbrushes in that they impart movement to the bristles at much higher speeds than possible manually. They also may impart different types and directions of motion. These motions, generally in combination with manual movement of the toothbrush by the user, provide superior cleaning than manual toothbrushes. Typically, powered toothbrushes are powered by disposable or rechargeable batteries that power an electric motor that in turn drives the toothbrush head.

Known powered toothbrushes include a brush head with a bristle carrier portion that rotates, oscillates or vibrates in some manner so as to clean the teeth. The bristles, which typically comprise bristle tufts, are generally uniform with one end fixed into the bristle carrier portion and the other end free to contact the surface of the teeth while brushing. The free ends of the various tufts present a surface envelope that is capable of some deformation when the bristles bend. When in contact with the surface to be brushed, the bristles may deform so that the surface envelope tends to conform to the complex surface of the teeth. Human teeth generally lie in a "C" shaped curve within the upper and lower jaws, and each row of teeth consequently has a convex outer curve and a concave inner curve. Individual teeth often have extremely complex surfaces, with areas that may be flat, concave, or convex. The more precise conformation between the bristles and the tooth surface, the more effective the toothbrush may be in cleaning, whitening and/or stimulating.

Known powered toothbrushes typically arrange the bristles in a compact conical or cylindrical pattern on a generally circular, disk-shaped bristle carrier. The powered toothbrush heads are traditionally compact, generally oval in shape and the heads are produced with a flat trimmed bristle pattern. Alternatively, other head shapes and bristle patterns are available.

One example of a powered toothbrush is depicted in U.S. Pat. No. 5,625,916 to McDougall, which is hereby incorporated by reference in its entirety. The toothbrush shown in McDougall has a disc-shaped bristle carrier. The bristle carrier, and thus the bristles, are driven in a vibrating or oscillating manner. This type of toothbrush is described herein with reference to FIGS. 1A-1C. A toothbrush 5 includes a handle portion 10 at a proximal end of the toothbrush 5 and a head 11 at a distal end of toothbrush 5. Handle portion 10 has compartments for containing a powered motor 14 and batteries 15 and 16. Head 11 includes a generally circular bristle holder (carrier) 13. A rotatable shaft 12 extends from motor 14 to head 11. A shaft coupling 17 may be located along shaft 12 and configured to provide for shaft 12 to be separated at a point between motor 14 and head 11. This permits the shaft to be removed from toothbrush 5, e.g. for cleaning, servicing, or replacement.

Head 11 includes a post 18 that provides a rotational pivot axis for bristle holder 13 containing bristle tufts 19. The distal end of shaft 12 has a journal or offset 20 that is radially displaced from the longitudinal axis of shaft 12, which may be integrally formed therewith. Bristle holder 13 has a slot 22 that receives offset 20. Offset 20 and slot 22 are configured so as to be oriented toward the intersection of shaft 12 axis and the longitudinal axis of post 18. When motor 14 rotates shaft 12, the motion of offset 20 defines a circle about shaft 12 axis and drivingly engages slot 22 such that bristle holder 13 vibrates or oscillates about post 18 axis through a rotational angle A. The rotational angle A is defined by the displacement of offset 20 from shaft 12 axis relative to the diameter of bristle holder 13.

Although powered toothbrushes such as those described immediately above provide advantages over manual toothbrushes, they are subject to various limitations. Providing a rotating or oscillating bristle holder (carrier) with a typical oblong or oval toothbrush head constrains the size of the moving bristle holder, and consequently the area of bristles available for teeth cleaning. Also, when the bristles are placed in contact with the teeth during brushing, there is less bristle contact with adjacent areas, such as the gums. Thus, while these compact bristle patterns provide for cleaning, there is minimal whitening and stimulation.

One attempt to overcome the limitations associated with a small powered bristle area is shown in U.S. Pat. No. 6,000,083 to Blaustein et al. The toothbrush in Blaustein et al. has a bristle area and pattern similar to a manual toothbrush, but an area of the bristles has simply been replaced by a powered bristle section. The result is that the head has a powered or moving bristle section and static bristle section. The limitation of Blaustein et al. is that the static bristle section provides no better cleaning, whitening or stimulation than a manual toothbrush.

International Application No. PCT/EP01/07615 of Braun GmbH discloses a powered toothbrush with two separate bristle parts that can move. Each bristle part can have a different range and/or type of motion. However, only one bristle part is powered. The other unpowered bristle part moves due to a resonance effect imparted by the frequency of the movement of the first bristle part.

This free resonance causes a number of difficulties. First, because any contact between the bristle parts will dampen or cancel any resonance of the unpowered bristle part, the unpowered bristle part "floats" separately from the powered bristle part. This necessitates separation or gaps between them. These gaps expose the internal workings of the head to foreign matter such as water, saliva, toothpaste, and food particles. This foreign matter may interfere with the workings of the unpowered bristle head. For example, the unpowered bristle part is spring-loaded to assist its resonance. Foreign matter may accumulate on or around the spring, interfering with its function. In addition, food particles may remain in the head and may fester and host microorganisms, which are undesirable if not potentially harmful when introduced directly into the mouth.

Another limitation of such a design is that movement of the unpowered bristle part may be damped by contact with the teeth, or lessened when the frequency of the powered part shifts from the resonance frequency. This can occur due to pressure imparted against the powered bristle part by the teeth or gums during brushing. Finally, the energy imparted to the unpowered bristle part is only a portion of the energy input into the powered part. Therefore, the unpowered bristle part is less effective in cleaning than the powered part, limiting the overall effectiveness of the toothbrush.

Thus, there is a need in the art for a powered toothbrush with increased effectiveness through a larger area of powered or driven bristles or bristles that are otherwise movable. There is also a need for a toothbrush having increased whitening and/or stimulation than known toothbrushes. There is further a need for such improved toothbrushes to be comparable in manufacturing and purchasing costs as known powered toothbrushes.

SUMMARY OF THE INVENTION

A powered toothbrush is provided and includes a handle portion at a proximal end and a head at a distal end with a neck being formed between the handle portion and the head. According to one embodiment, the head has two distinct movable parts that provide oral health benefits since each part is adapted to have a number of bristles or elastomeric cleaning members or a combination thereof extending therefrom to contact surfaces of the teeth and surrounding areas. The toothbrush has a drive mechanism that imparts movement to one of the movable parts to deliver a cleaning, polishing, whitening action that supplements the cleaning efficiency of a typical powered toothbrush.

In one exemplary embodiment, the first movable head part is a first bristle carrier that supports a number of bristle tufts, elastomeric cleaning members, or a combination thereof. The first bristle carrier is operatively mounted to the head and is coupled to the drive mechanism such that the first bristle carrier oscillates back and forth in a direction about a center point of the first bristle carrier. Preferably, the oscillating first bristle carrier is moved back and forth in a rotational direction. The second movable part is a second bristle carrier in the form of an elastomeric "shock-absorbing" member that is operatively mounted to the head and includes a number of bristle tufts, elastomeric cleaning members, or combination thereof, extending outwardly therefrom. During a brushing action, forces are applied against the second carrier and the elastomeric nature of the second bristle carrier causes the earner to move in a substantially up and down manner to deliver additional oral health benefits including enhanced cleaning, tooth polishing and/or tooth whitening.

Other features and advantages of the present invention will be apparent from the foregoing detailed description when read in conjunction with the accompanying drawings.

The invention accordingly comprises the several steps and the relation of one or more of such steps with respect to each of the others, and the apparatus embodying features of construction, combination(s) of elements and arrangement of parts that are adapted to effect such steps, all as exemplified in the following detailed disclosure, and the scope of the invention will be indicated in the claims.

BRIEF DESCRIPTION OF THE DRAWING FIGURES

For a more complete understanding of the invention, reference is made to the following description and accompanying drawings, in which.

DETAILED DESCRIPTION OF PREFERRED EMBODIMENTS

Figure 1A:
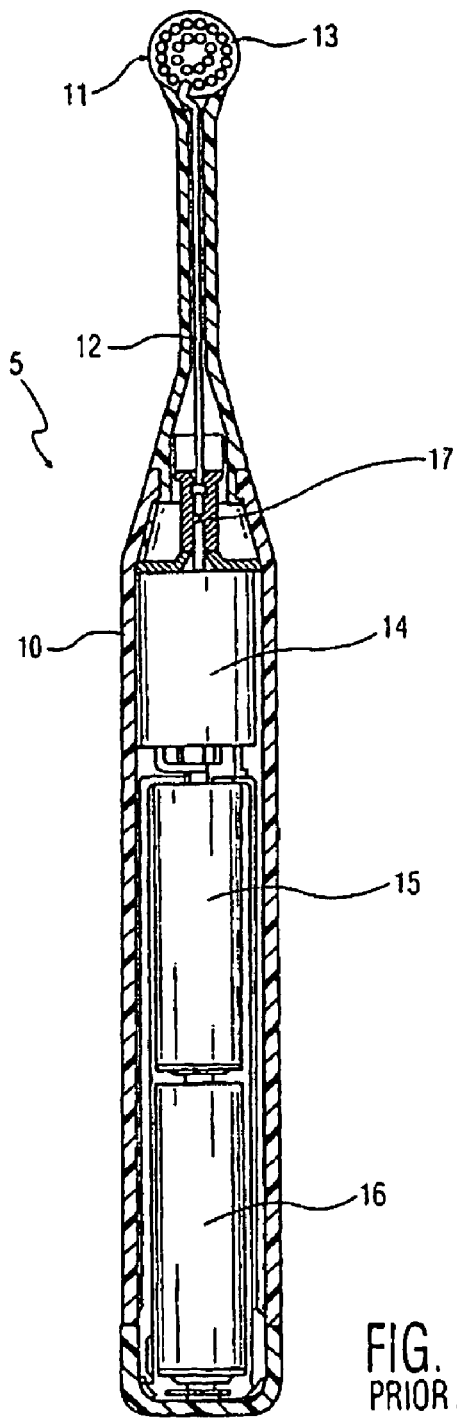
FIG. 1A is a front cross-sectional view of a conventional powered toothbrush including a head.

Referring first to FIGS. 2 through 5 in which an exemplary powered toothbrush according to a first embodiment is illustrated and generally indicated at 100. Toothbrush 100 includes a handle 102 at a proximal end thereof that defines an interior compartment (not illustrated) for housing various toothbrush components, and a brush section 104 that is defined by a neck 106 that terminates in a head 120 at a distal end of toothbrush 100. Handle 102 has a free proximal end 108 and an opposite neck end 110. Neck 106 generally extends from a first end 112 to a second end 114 with the first end 112 being located at neck end 110 of handle 102 and second end 114 being located at head 120. In other words, neck 106 is the portion of toothbrush 100 that extends between handle 102 and head 120. Neck 106 also defines an interior compartment (not illustrated) for housing various working components of toothbrush 100. Head 120 is preferably generally aligned with the longitudinal axis of the toothbrush 100.

According to one embodiment, neck 106 and handle 102 may be constructed as a unitary member by forming neck 106 integral to handle 102 at the end 110 of handle 102. In another embodiment, neck 106 is detachable from handle 102 at end 110 of neck 106. In accordance with this detachable embodiment, combined neck 106 and head 120 can be removed from handle 102 to permit cleaning, servicing and/or interchanging of either handle 102 or combined neck 106 and head 120 (brush section 104). When neck 106 is formed to be detachable from handle 102, first neck end 112 preferably includes a connector linkage (not shown) that is adapted to be detachably joined to handle 102 using traditional techniques. It will also be appreciated that the point of detachment can be between head 120 and neck 106 such that head 120 is of a refill head type.

It will further be appreciated that the illustrated shapes of handle 102 and neck 106 are merely exemplary in nature and handle 102 and/or neck 106 can be formed to have any number of shapes. Preferably, the shapes of handle 102 and neck 106 are ergonomically pleasing to a user of toothbrush 100 and provide a toothbrush which is easily gripped and held and easily manipulated by the user. For example, handle 102 can include slightly recessed finger sections 118 which are formed on opposite sides of handle 102. One recessed finger section 118 is designed to receive the thumb of one hand and the other recessed finger section 118 is designed to receive one or more other fingers of the same hand to thereby assist the user in proper placement of toothbrush 100 in the user's hand. One or more of the recessed finger sections 118 can include ribs or another type of roughened surface to assist the user in gripping the toothbrush in the recessed finger sections 118.

Head 120 of the toothbrush 100 includes a head base 160 that partially defines an inner compartment 121 of head 120. Head base 160 may be constructed so that it terminates in a rounded distal end 162, which defines the distal end of toothbrush 100. Preferably, head base 160 is integrally attached to second end 114 of neck 106.

Figure 1B:
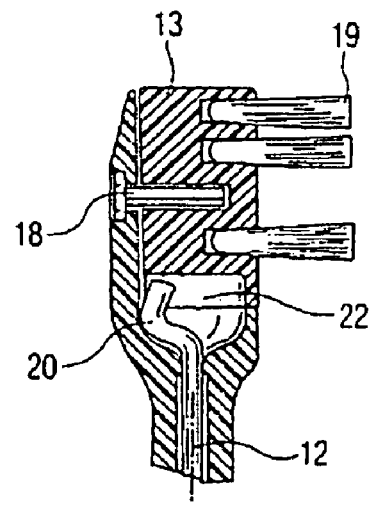
FIG. 1B is a partial side cross-sectional view of the toothbrush head of FIG. 1A.
Figure 1C:
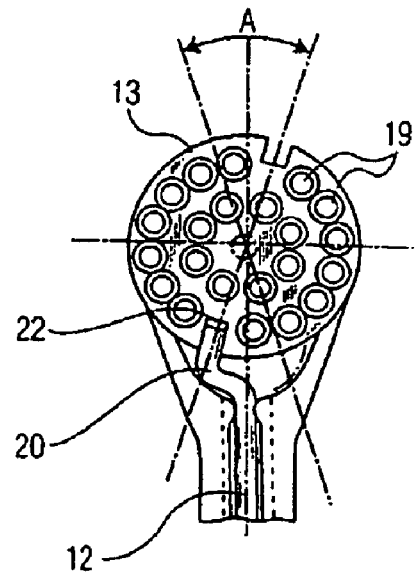
FIG. 1C is a partial front cross-sectional view of the toothbrush head of FIG. 1A.

Head 120 also includes a first movable bristle carrier 180 which is illustrated as being at the outermost or distal portion of head 120. First bristle carrier 180 may have a construction that is either identical to or similar to that of bristle holder 12 illustrated in FIGS. 1A-1C. First movable bristle earner 180 is preferably formed as a disk having a circular cross-section since it is intended to oscillate in a rotational manner about a center point thereof. However, it will be appreciated that first movable bristle carrier 180 is not limited to having a disk shape and can have any number of different shapes, such as an oval or various other regular or irregular shapes, so long as bristle carrier 180 is able to oscillate in a substantially rotational manner. A circular shape is preferred since it requires the least amount of clearance to accommodate the oscillating movement.

A plurality of tooth care elements 152 are coupled to and extend outwardly positioned perpendicular to the direction of oscillation of first movable bristle carrier 180 (shown in phantom in FIG. 4) and substantially perpendicular to a plane defined by a surface of head 120 opposite tooth care elements 152 and bristle carrier 180. As used herein, the term "tooth care elements" includes any type of structure that is commonly used or is suitable for use in providing oral health benefits (e.g., tooth cleaning, tooth polishing, tooth whitening, etc.) by making intimate contact with surfaces of the teeth and surrounding areas. Such tooth care elements include but are not limited to tufts of bristles that can be formed to have a number of different shapes and sizes and elastomeric members (see FIGS. 13-17) that can be formed to have a number of different shapes and sizes, or a combination of both. Bristle tufts arranged on first bristle carrier 180 are only one exemplary configuration and it will be understood that other bristle configurations (such as stapled, IMT, etc.) can be used and the bristle tufts can be formed of the same or different bristle materials (such as nylon bristles, spiral bristles, rubber bristles, etc.). Moreover, while the tooth care elements can be arranged so that they are generally perpendicular to the plane defined by the opposite surface of head 120 from the tooth care elements, some or all of the tooth care elements may be angled at various angles with respect to first movable bristle carrier 180. When the first movable bristle carrier 180 includes bristle tufts, it is thereby possible to select the combination of bristles configurations, bristle materials and bristle orientations to achieve specific intended results, such as to create as much movement from the moving tuft heads to deliver additional oral health benefits like enhanced cleaning, tooth polishing and/or tooth whitening.

While first movable bristle carrier 180 has been defined as a movable bristle earner 180, it will be understood that first movable carrier 180 is not limited to having only tufts of bristles as a part thereof. Instead, first movable bristle carrier 180 is to be broadly considered as being a carrier for any number of suitable tooth care elements or any number of combinations of different types of tooth care elements. For example, first movable bristle carrier 180 can include a number of elastomeric members to provide the desired oral health benefits. The elastomeric members can be attached to first movable bristle carrier 180 using conventional techniques, including integrally forming the elastomeric members with an upper surface of carrier 180. The tooth care elements provided as part of the first movable bristle carrier 180 can thus be entirely of one type (e.g., bristle tufts or elastomeric members) or can be a mixed arrangement.

Figure 13:
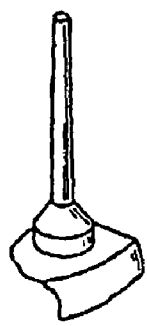
FIG. 13 is a perspective view of an elastomeric tooth care element having a first configuration and adapted for use in the toothbrush head constructed in accordance with the invention.
Figure 14:
FIG. 14 is a perspective view of an elastomeric tooth care element having a second configuration and adapted for use in the toothbrush head constructed in accordance with the invention.
Figure 15:
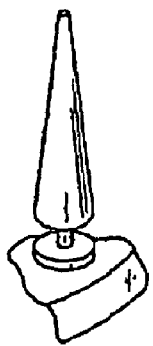
FIG. 15 is a perspective view of an elastomeric tooth care element having a third configuration and adapted for use in the toothbrush head constructed in accordance with the invention.
Figure 16:
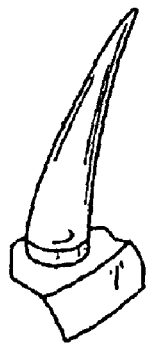
FIG. 16 is a perspective view of an elastomeric tooth care element having a fourth configuration and adapted for use in the toothbrush head constructed in accordance with the invention.
Figure 17:
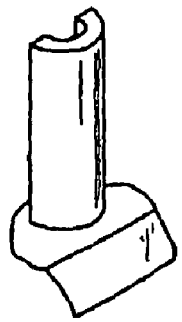
FIG. 17 is a perspective view of an elastomeric tooth care element having a fifth configuration and adapted for use in the toothbrush head constructed in accordance with the invention.

FIGS. 13-17 illustrate various exemplary elastomeric members that can serve as tooth care elements 152. FIG. 13 shows an elastomeric tooth care element in the form of a thin spike; FIG. 14 shows an elastomeric tooth care element in the form of a barrel spike; FIG. 15 shows an elastomeric tooth care element in the form of a squeegee point; FIG. 16 shows an elastomeric tooth care element in the form of an angled point; and FIG. 17 shows an elastomeric tooth care element in the form of a section of an elastomeric wall. The elastomeric wall of FIG. 17 may be formed with a linear, planar shape; a zigzag shape; a serpentine shape, etc. All of the above elastomeric tooth care elements can have smooth textures or can have rough surfaces. In addition, the wall sections of the elastomeric tooth care elements can be vertically straight, taper toward inward toward one end or expand toward one end. The tops of the elastomeric tooth care walls can have a planar surface or can have a protrusion (i.e., hump) or the like formed thereat.

For purpose of illustration only, first movable bristle carrier 180 will be described as containing a predetermined number of bristle tufts; however the following features apply equally to the situation where first movable bristle carrier 180 is formed entirely or partly of elastomeric members. The bristle tufts of first movable bristle carrier 180 can have uniform heights or non-uniform heights. For example, first movable bristle earner 180 can include bristle tufts having a first height and bristle tufts having a second different height.

First movable bristle earner 180 is constructed so as to pivotally rotate about a center point thereof, thereby effectuating movement of the bristle tufts and/or elastomeric members that extend outwardly from the plane defined by the face positioned perpendicular to the direction of oscillation of first movable bristle carrier 180. The movement of first movable bristle earner 180 is preferably an oscillation type movement as the first movable bristle carrier 180 pivots about a post at a center point thereof (see FIG. 1). First movable bristle carrier 180 is formed with a slot or opening (not shown). This slot is preferably identical or substantially similar to slot 22 illustrated in FIGS. 1A-1C. Preferably, slot 22 is formed at a peripheral edge of first movable bristle carrier 180 and extends along a substantial height of first movable bristle carrier 180. For example, slot 22 preferably does not extend to the upper surface of first bristle carrier 180 where the tooth care elements are formed. Instead, slot 22 preferably has a closed upper end to prevent foreign matter, such as saliva, toothpaste, foreign particles, etc. from entering the slot when the operator is performing a brushing operation. The opposite end of the slot, which is located within inner compartment 121 of head 120, can be open.

Toothbrush 100 includes a drive mechanism to effectuate movement of certain parts of toothbrush 100 and more specifically, for causing movement of at least first movable bristle carrier 180. One exemplary drive mechanism is disclosed in U.S. Pat. No. 5,625,916 to McDougall, which has been previously incorporated herein by reference and includes a rotating drive shaft 200 that extends at least through neck 106 (i.e., the inner compartment thereof). Drive shaft 200 preferably has a construction identical to or substantially similar to drive shaft 12 illustrated in FIGS. 1A-1C.

Drive shaft 200 has one end (not shown) that is operatively connected to a drive member (not shown), such as a motor or any other type of drive device, for imparting movement to first movable bristle carrier 180. Drive shaft 200 is formed with an opposing distal end (not shown) that is bent such that the end is not axially aligned with the longitudinal axis of drive shaft 200. This distal bent may be formed with a shape identical to or substantially similar to end 20 illustrated in FIGS. 1A-1C or may be formed differently according to another construction so long as it performs the intended function. In other words, the end is an offset crank end of drive shaft 200 and is configured to be received in slot 22 so that the 360° rotational movement of shaft 200 is transmitted into an oscillating back and forth rotational movement of first movable bristle carrier 180.

The drive mechanism for powered toothbrush 100 can be any type of drive, e.g. a rotating drive, an oscillating drive, an eccentric drive, an unbalanced-generated drive, a drive having one more gearing mechanisms, or any other type that is capable of performing the intended function. The drive mechanism can be realized in the form of an electric motor or other type of motor and the movement generated by the drive can be imparted to one or more sections of head 120 or to other elements that can be present at the brush section, such as bristle tufts, elastomeric members. The movement can be imparted directly through a driving axle, such as drive shaft 200 or it can be imparted through a driving post attached to the driving axle. When toothbrush 100 includes an oscillating drive mechanism either identical to or similar to the exemplary drive mechanism illustrated in FIGS. 1A through 1C, the interior compartment of handle 102 houses a motor operatively connected to drive shaft 200 and a source to power the motor, such as one or more batteries.

When the drive mechanism is actuated and drive shaft 200 is rotated, the movement of the crank end imparts an oscillating back and forth movement of first movable bristle earner 180 through an angle between about 10° to about 120° and in a preferred exemplary embodiment, the movement is through an angle between about 10° to about 30° and in a most preferred embodiment is through an angle between about 10° to about 15°.

Toothbrush 100 further includes a second movable bristle carrier 210 that is operatively mounted on head 120. Second movable bristle carrier 210 is formed of an elastomeric material and is generally formed in the form of a head section that has a range of movement when forces are applied to it during normal operation and/or normal use of toothbrush 100. Elastomeric second bristle carrier 210 has a first end 212 that is disposed in close proximate relation to the first bristle carrier 180 and an opposing second end 214 that is disposed at or near the proximal end of head 120. Elastomeric second bristle carrier 210 further includes a first side 216 and a second side 218 with a recessed section 220 being defined thereby between first and second ends 212, 214 and first and second sides 218, 220. Recessed section 220 defines a recessed compartment that has a floor 222.

Figure 4:
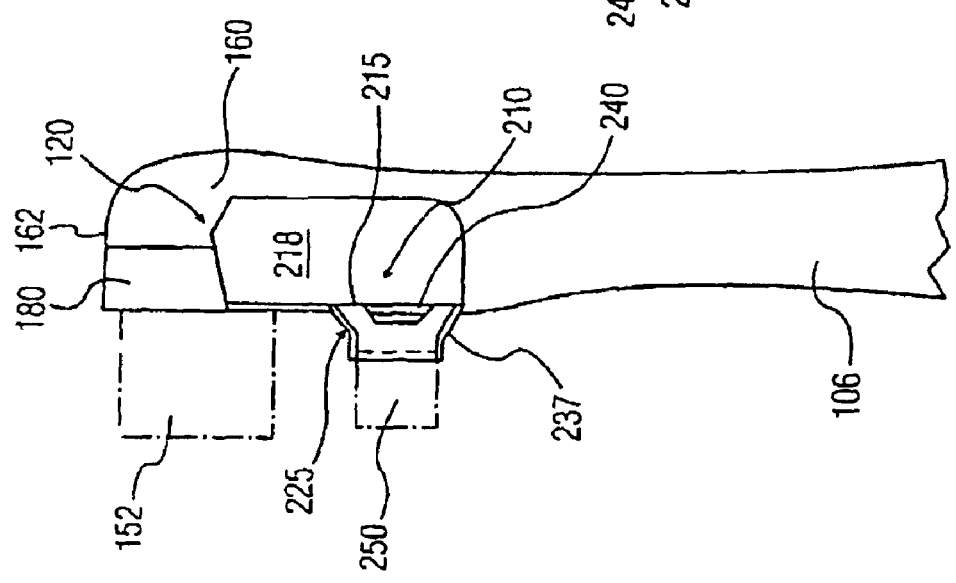
FIG. 4 is a side elevational view of the toothbrush head of FIG. 2.

According to one exemplary embodiment, elastomeric second bristle carrier 210 is supported only at first side 216 and second side 218, respectively, by head base 160 such that elastomeric second bristle carrier 210 extends across inner compartment 121 of head 120 and is formed as a substantially "floating" elastomeric platform. The attachment of elastomeric second bristle carrier 210 to head base 160 can be accomplished using conventional techniques, such as using an adhesive, providing a mechanical bond, or integrally attaching the two members during a molding operation. In one embodiment, the side walls of the head base 160 may be formed with cut-away portions (i.e. U-shaped in the illustrated embodiment) that receive the first and second sides 216, 218, which are formed as side walls that are received in the cut-away portions of head base 160, as best shown in FIG. 4.

Because first bristle carrier 180 is preferably formed in the shape of a disk, first end 212 is preferably formed with an arcuate shape to accommodate the oscillating back and forth rotational movement of first bristle carrier 180. Second end 214 may also be formed with an arcuate shape, as illustrated, or it may be formed with any other shape. Second end 214 preferably forms a butt joint with the distal end of neck 106, or second end 214 may be adapted to extend slightly over the distal end of neck 106 if additional support of second end 214 is desired. Elastomeric second bristle carrier 210 is also formed with a lower surface 215 that extends across inner compartment 121 of head 120. Lower surface 215 is therefore coupled to upper edges of the side walls of head base 160 in this region of head 120, thereby permitting shaft 200 to extend underneath lower surface 215 through inner compartment 121 to the slot in first carrier 180.

A bristle holder 230 is securely disposed within recessed section 220 defined by elastomeric second bristle carrier 210 and is designed to hold a number of tooth care elements 152, such as bristle tufts, elastomeric members or a combination thereof. Accordingly, the shapes of bristle holder 230 and the recessed section 220 must be complementary to one another. In the illustrated embodiment, each of the bristle holder 230 and the recessed section 220 has an annular shape; however, each can have any regular shape or irregular shape (e.g. square, oval, diamond, rectangle, etc.) Bristle holder 230 supports one or more, and preferably a plurality of tooth care elements, generally illustrated at 250, which extend outwardly from a plane parallel to a face thereof. It will be appreciated that bristle holder 230 can hold any number of different types of tooth care elements and is not limited to merely support bristle tufts, since elastomeric members can equally be held by bristle holder 230 or be formed at part thereof. Bristle holder 230 is preferably a relatively rigid member that is formed of a suitable material, such as a plastic, that will provide the desired structural characteristics. However and according to an alternative embodiment, bristle holder 230 may be formed of an elastomeric material that can have a rigidity less than, equal to, or greater than the rigidity of the elastomeric material forming elastomeric second bristle carrier 210.

Elastomeric second bristle carrier 210, including the bristle holder 230, can be formed using conventional manufacturing methods. In one embodiment, elastomeric second bristle carrier 210 is formed around bristle holder 230 in a conventional molding process where bristle holder 230 is first positioned and properly located within a mold and then elastomeric material is injected around bristle holder 230 to thereby form the elastomeric portion of bristle carrier 210 around bristle holder 230.

Elastomeric second bristle carrier 210 is preferably formed such that bristle holder 230 lies in a plane that is above head base 160, and more preferably above an upper surface of neck 106. Elastomeric second bristle carrier 210 therefore includes a built-up section (raised section) 225 above the upper surface of neck 106 which leads to an upper face 231 of bristle holder 230. In an exemplary embodiment, the built-up section includes a radial shoulder 237 that extends around bristle holder 230. Elastomeric second bristle carrier 210 thus ramps upwardly from the upper surface of neck 106 to upper face 231 and then carrier 210 ramps downwardly toward first bristle carrier 180. The recess 220 is preferably defined by raised section 225.

Figure 2:
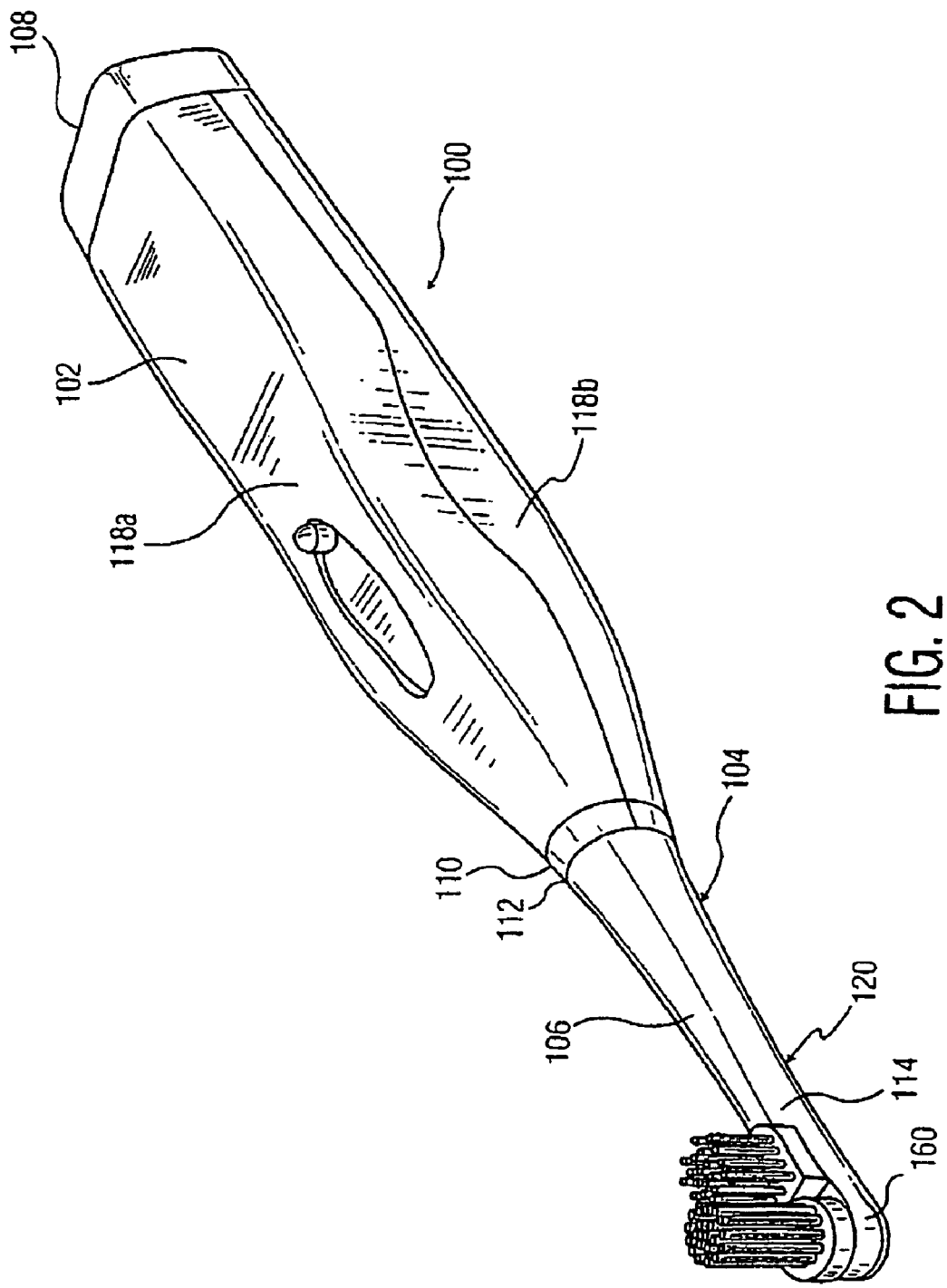
FIG. 2 is a front and side perspective view of a powered toothbrush according to one exemplary embodiment of the invention showing a toothbrush head having distinct first and second movable carrier sections constructed in accordance with the invention.
Figure 5:
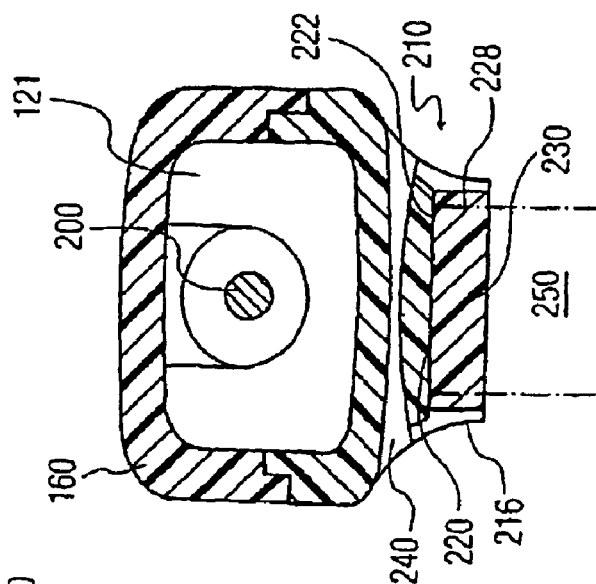
FIG. 5 is a cross-sectional view taken along the line 5-5 of FIG. 3.
Figure 3:
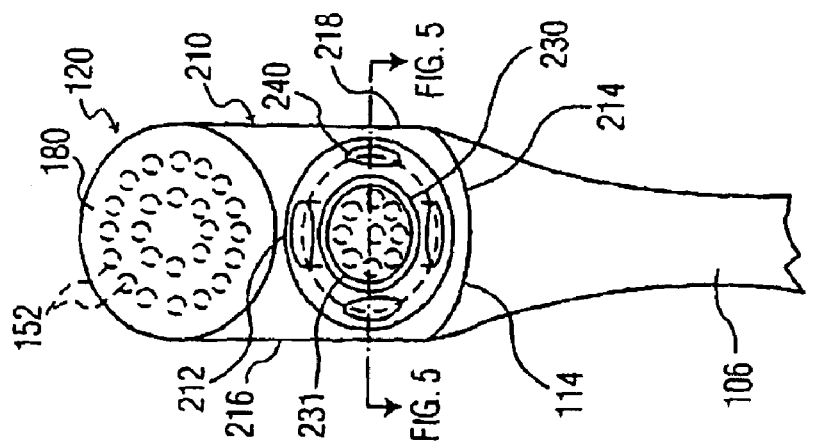
FIG. 3 is a front elevational view of the toothbrush head of FIG. 2.
Figure 6:
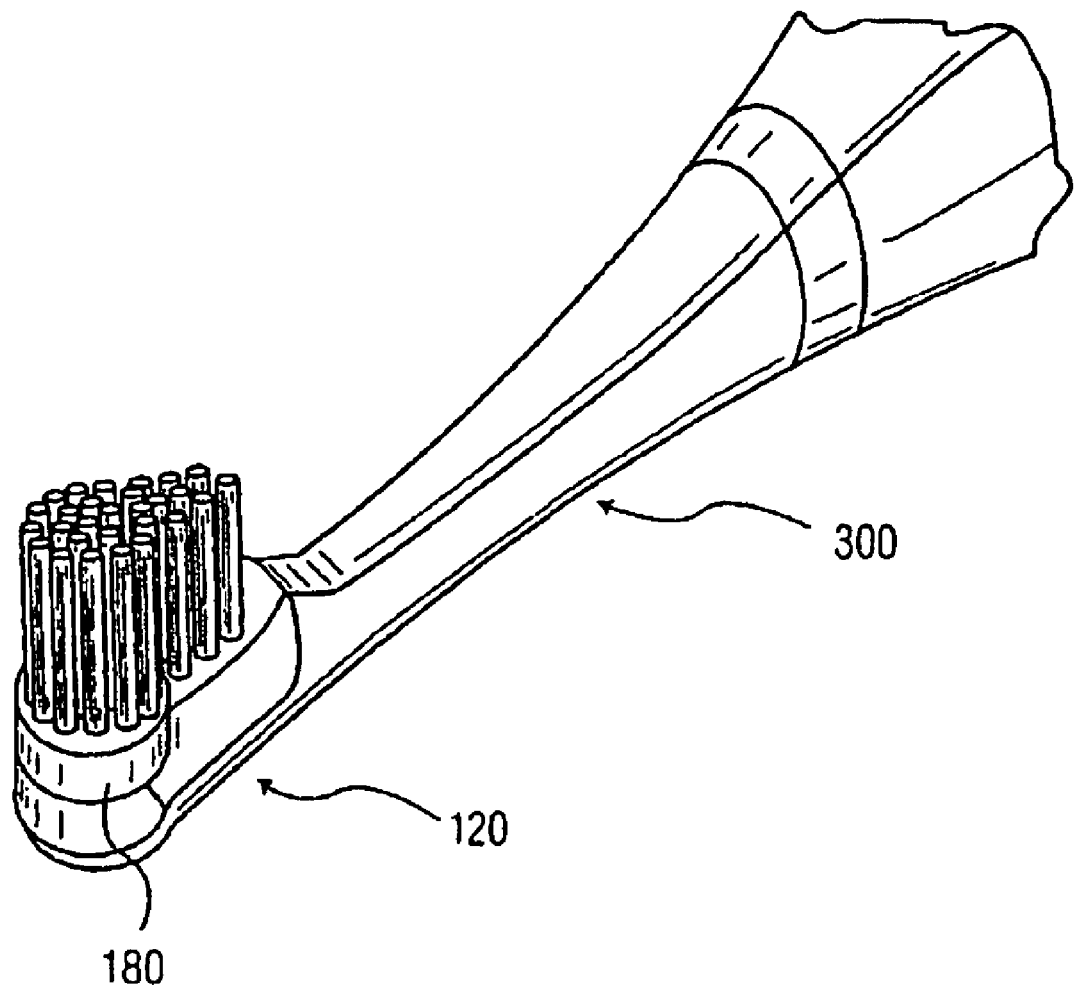
FIG. 6 is a front and side perspective view of a powered toothbrush head according to another exemplary embodiment of the invention showing a toothbrush head having distinct first and second movable carrier sections constructed in accordance with the invention.

Elastomeric second bristle carrier 210 also defines a cavity or a hollow channel (e.g., a through hole) 240 extending from first side 216 to the second side 218 thereof. As best shown in the side elevation view of FIG. 4 and the cross-sectional view of FIG. 5, cavity 240 is defined underneath bristle holder 230, a top boundary of the cavity being defined by an amount of elastomeric material disposed adjacent the bottom surface of the bristle holder 230. Cavity 240 is also preferably positioned above the side walls of the head base 160 to permit cavity 240 to be free of all obstructions and permit the operator to see clearly through cavity 240. In another embodiment, cavity 240 does not have open ends; but rather, its sides are defined by an enclosed pocket underneath bristle holder 230; or it can be formed so that only one end is open. Optionally (as best illustrated in FIGS. 2 and 3), a second cavity or hollow channel (e.g., through hole) 240 is defined and extends longitudinally from first end 212 to the second end 214. In this embodiment, the two channels intersect in a central portion of second bristle carrier 210. It will be appreciated that the cavity 240 does not have to extend completely through second bristle carrier 210.

Cavity 240 acts as a shock absorbing pocket and permits the elastomeric second bristle carrier 210 to move substantially vertically (up and down) when a force is applied to elastomeric second bristle carrier 210. More specifically, when a force is applied to an upper surface of carrier 210 (e.g. to upper face 231), elastomeric second bristle carrier 210 is compressed downward due to the deformation or partial collapse of carrier 210 about cavity 240.

Because of its elastomeric nature, second bristle carrier 210 is restored to its relaxed condition when the applied force is removed. In other words, once the applied force is removed, cavity 240 assumes its initial shape, thereby imparting shock absorbing characteristics to second bristle earner 210. It will be appreciated that by altering the dimensions of cavity 240, the shock absorbing characteristics of second bristle carrier 210 can be varied. For example, as the dimensions of cavity 240 are increased, carrier 210 will deform more easily upon application of a force. This directly translates into added substantially vertical movement of elastomeric second bristle carrier 210 as the operator of toothbrush 100 brushes his or her teeth and the tooth care elements (bristles and/or elastomeric members) extending from bristle holder 230 contact teeth and surrounding areas. A normal brushing action will impart a number of forces at different angles against elastomeric second bristle carrier 210.

Moreover, the elastomeric characteristics of second bristle carrier 210 can be further altered by the definition of one or more apertures 250 in second bristle carrier 210 by bristle holder 230. The apertures serve to increase the resiliency of second bristle carrier 210 since the definition of apertures 250 results in removal of elastomeric material.

In yet another embodiment, an upper section of second bristle carrier 210 defines a hollow, deformable dome-like structure. Bristle holder 230 defines an upper surface of the dome-like structure, and also defines at least one aperture therein to let air in and out of the cavity defined by bristle holder 230. Thus, when a force is applied to bristle holder 230, as during a brushing action, the dome-like structure at least partially collapses as air in the cavity is evacuated through the at least one aperture.

The elastic motion of elastomeric second bristle carrier 210 delivers additional oral health care benefits such as enhanced cleaning, tooth polishing, and/or tooth cleaning since second bristle carrier 210 has a number of tooth care elements extending therefrom for contacting the gingival surfaces during a brushing action. It will be understood that tooth care elements can be located in other areas besides bristle holder 230. For example, some tooth care elements can be attached to and extend upwardly from the top face of carrier 210 surrounding bristle holder 230.

Referring next to FIGS. 6-12, an elastomeric second bristle carrier according to another embodiment of the invention is illustrated and generally indicated at 300. In accordance with this embodiment, elastomeric second bristle carrier 300 does not include a bristle holder (such as bristle holder 230 of FIG. 5). Rather, elastomeric second bristle carrier 300 is generally formed as a "floating" head section that has a range of movement when forces are applied to it during normal operation and/or normal use of toothbrush 100. Elastomeric second bristle carrier 300 is formed with a first end 302 that is disposed in close proximate relation to first bristle carrier 180 and an opposing second end 304 that is disposed at or near the proximal end of head 120. Elastomeric second bristle carrier 300 further includes a first side 306, an opposing second side 308, an upper surface 310 and a lower surface 312 that faces inner compartment 121. Upper surface 310 is preferably not a planar surface but rather is an arcuate surface (e.g. a convex shaped surface).

According to one exemplary embodiment, elastomeric second bristle carrier 300 is only supported at first side 306 and second side 308, respectively, by head base 160 such that elastomeric second bristle carrier 300 extends across and therefore defines an upper limit of inner compartment 121 of head 120 and is therefore formed substantially as a "floating" elastomeric platform. The attachment of elastomeric second bristle carrier 300 to head base 160 can be accomplished using conventional techniques, such as using an adhesive, providing a mechanical bond, or integrally attaching the two members during a molding operation. Because first bristle carrier 180 is formed preferably in the shape of a disk, first end 302 preferably is formed with an arcuate shape to accommodate the oscillating back and forth rotational movement of first bristle earner 180. Second end 304 can also be formed with an arcuate shape, as illustrated, or it can be formed with any other shape. Second end 304 preferably forms a butt joint with the distal end of neck 106 or second end 304 can extend slightly over the distal end of neck 106 if additional support of second end 304 is desired. Lower surface 312 is therefore coupled to upper edges of the side walls of head base 160 in this region of head 120, thereby permitting shaft 200 to extend underneath lower surface 312 and through the inner compartment 121 to the slot in first bristle carrier 180.

Second bristle carrier 300 defines an enlarged cavity, hollow channel (e.g. through hole) or pocket 320 that extends not only from side 306 to side 308 but it is also defined so that it extends substantially from the first end 302 to the second end 304. Cavity 320 is defined above the upper side edges of head base 160 that serve as points for attachment between head 120 and second bristle earner 300. Second bristle carrier 300 is further formed with a weakened section incorporated therein to facilitate movement of second bristle carrier 300 upon application of a force to upper surface 310. For example, a longitudinal or transverse groove (i.e., a score) 330 may be defined in at least one of upper surface 310 and a surface 317 defining an upper limit of cavity 320. In the illustrated embodiment, a single groove 330 is formed across surface 317. Groove 330 forms a weakened section longitudinally within second bristle carrier 300 (a so called "living hinge" is formed). It will be appreciated that groove 330 can equally be formed longitudinal from first end 302 to second end 304.

Figure 9:
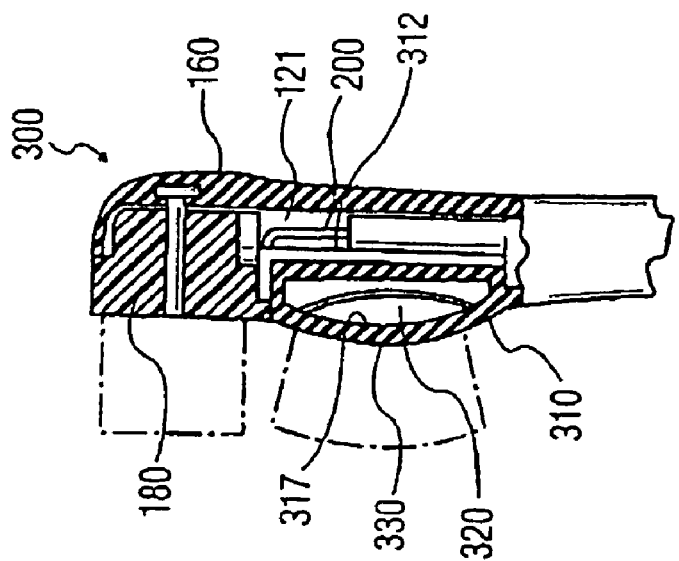
FIG. 9 is a cross-sectional view taken along the line 9-9 of FIG. 7 with parts broken away to illustrate an elastomeric carrier in a relaxed condition.
Figure 8:
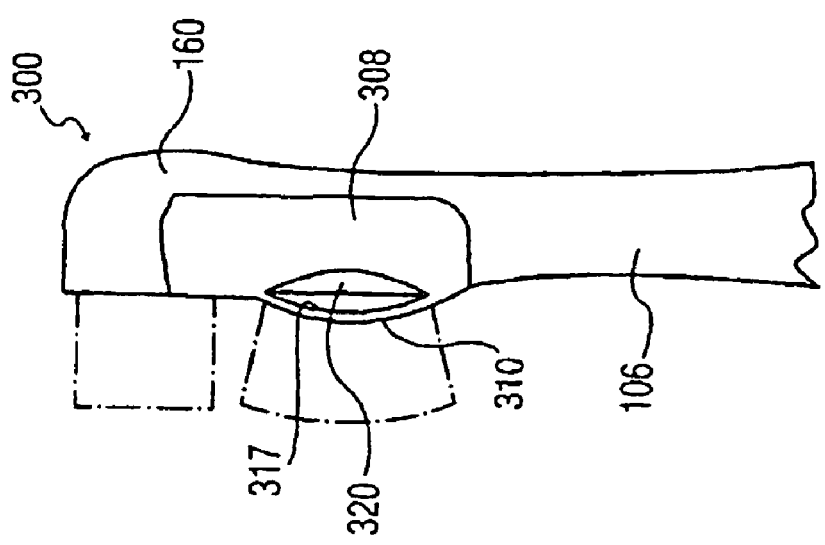
FIG. 8 is a side elevational view of the toothbrush head of FIG. 7.
Figure 7:
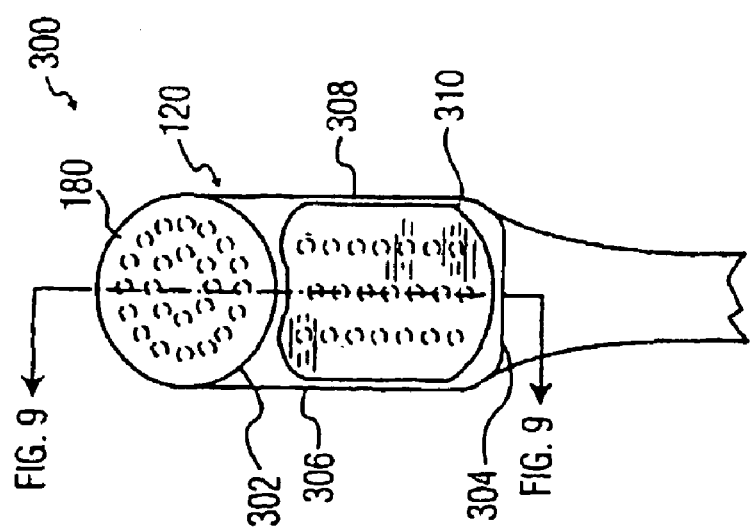
FIG. 7 is front elevational view of a toothbrush head according to another exemplary embodiment constructed in accordance with the invention.
Figure 12:
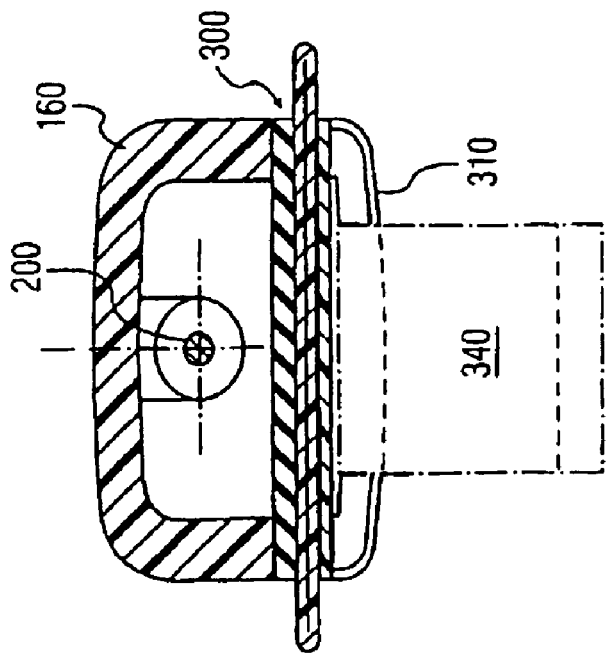
FIG. 12 is a cross-sectional view taken along the line 12-12 of FIG. 10.
Figure 11:
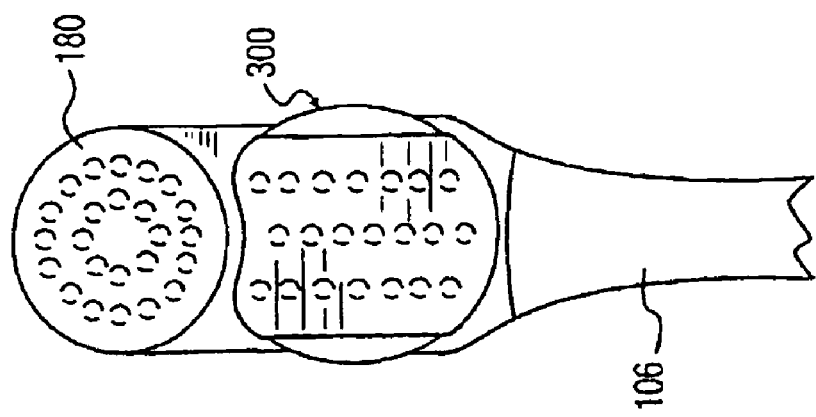
FIG. 11 is a front elevational view of the elastomeric carrier of FIG. 10 in the depressed condition.
Figure 10:
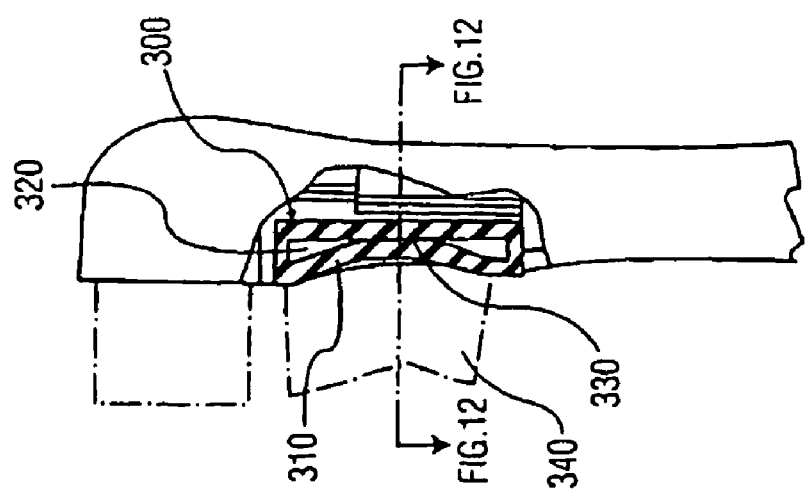
FIG. 10 is a side elevational view with parts broken away to illustrate the elastomeric carrier of FIG. 9 in a depressed condition.

The cross-section of FIG. 9 illustrates second bristle carrier 300 in a relaxed condition prior to application of a force to upper surface 310. FIGS. 10-12 illustrate the second bristle carrier 300 in deformed condition after a force is applied to upper surface 310. When a force is applied to upper surface 310, upper surface 310 deforms about the living hinge created by one or more grooves 330. This results in upper surface 310 at least partially collapsing along the living hinge section. Tooth care elements 340 formed on upper surface 310 flex inwardly toward one another as a result of such deformation, as illustrated in FIG. 10. Elastomeric second bristle carrier 300 can thus be thought of as a hinged block that has shock absorbing characteristics. When the applied force is removed, second bristle carrier 300 returns to its relaxed condition due to its elastomeric nature.

Preferably, tooth care elements 340 that extend upwardly from upper surface 310 are a plurality of elastomeric members (such as those shown in FIGS. 13-17) that are formed integrally with elastomeric second bristle carrier 300. For example, tooth care elements 340 can be formed in the same molding operation that forms elastomeric second bristle carrier 300. Thus, while elastomeric second bristle carrier 300 is described as a bristle carrier, it will be understood that the carrier 300 does not necessarily include any bristle tufts.

It will also be appreciated that in any of the foregoing embodiments, the toothbrush head can have a number of static tooth care elements disposed thereat in a number of different locations.

A powered toothbrush made in accordance with any of the present embodiment offers a number of advantages over conventional powered toothbrushes that are presently available. Movable first bristle carrier 180 oscillates back and forth, or moves otherwise, and as the operator brushes his or her teeth, the oscillating tooth care elements (i.e. bristle tufts and/or elastomeric members) contact the surfaces of the teeth and the surrounding areas to deliver enhanced cleaning, tooth polishing and/or tooth whitening. Elastomeric second bristle carriers 210, 300 permit tooth care elements to be disposed in a number of different patterns and the increased number of moving tooth care elements provide increased contact with gingival tissues and enhanced massaging thereof.

Toothbrush 100 according to the various embodiments disclosed herein can be made from any number of materials that are suitable for use in oral care products, such as toothbrushes, etc. For example, many of the components that are included in toothbrush 100 are formed of plastic materials. Accordingly, handle 102 and head 120 of powered toothbrush 100 can be molded from polyolefins such as polypropylenes and polyethylenes, polyamids such as nylons, and polyesters such as polyethylene terephthalate. Other suitable materials include polymethylmethacrylate, styrene acroylonitrate and cellulose esters, for example cellulose propionate. In addition, natural and synthetic rubbers can be used.

When the tooth care elements are in the form of tufts of bristles, the bristles of can be made from a flexible material suitable for dental hygiene. Generally, materials suitable for bristles are polyamides such as nylon or polyesters such as polybutylene terephthalate. When the tooth care elements are in the form of elastomeric members, they can be made from any number of suitable elastomeric materials, such as a block copolymer. Preferred block copolymers include styrenes (for example styrene ethylene butadiene styrene, or styrene butadiene styrene), polyolefins (for example polypropylene/ethylene propylene diamine modified systems (i.e. synthetic rubber)), polyamides (for example polyamide (2 or polyamide 6), polyesters (for example polyester ester or polyether ester), polyurethanes (for example polyesterurethane, polyetherurethane or polyesteretherurethane). In addition, natural rubbers or synthetic rubbers can be used.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A powered toothbrush comprising:
   a handle portion having a neck formed at one end; and
   a head coupled to the neck, the head including:
      a first carrier coupled to the head and operatively connected to a drive mechanism for moving the first carrier in a first path of motion, the first carrier having at least one of a plurality of bristles and an elastomeric cleaning member extending outwardly therefrom; and a second carrier coupled to the head, the second carrier being formed of an elastomeric material and having at least one of a plurality of bristles and an elastomeric cleaning member extending outwardly from an upper surface of the second carrier, the second carrier having a weakened section comprising a longitudinal or transverse groove such that upon application of a force to the upper surface thereof, the upper surface at least partially collapses resulting in movement of the at least one of a plurality of bristles and the elastomeric cleaning member, and upon removal of the force, the second carrier substantially returns to a non-collapsed condition.

2. The powered toothbrush of claim 1, wherein the first path of motion is about an axis perpendicular to an outer surface of the head.

3. The powered toothbrush of claim 2, wherein the first carrier oscillates in a rotational direction about a center point of the first carrier.

4. The powered toothbrush of claim 1, wherein the first carrier oscillates in a rotational direction about a center point of the first carrier.

5. The powered toothbrush of claim 1, wherein the second carrier moves substantially in a direction perpendicular to an outer surface of the head when the force is applied thereto.

6. The powered toothbrush of claim 1, wherein the drive mechanism includes a motor driven shaft having a drive end that drives the first carrier.

7. The powered toothbrush of claim 1, wherein the second carrier includes a body portion having an upper wall that includes the upper surface and an opposing lower wall, wherein the weakened section is formed in the upper wall.

8. The powered toothbrush of claim 4, wherein the groove extends perpendicular to a longitudinal axis of the head.

9. The powered toothbrush of claim 1, wherein the groove extends parallel to a longitudinal axis of the head.

10. The powered toothbrush of claim 1, wherein the second carrier defines a collapsible cavity formed between the upper surface and a lower surface thereof.

11. The powered toothbrush of claim 1, wherein the longitudinal or transverse groove is disposed in the upper surface of the second carrier.

12. A powered toothbrush comprising:
a handle portion having a neck formed at one end; and
a head coupled to the neck, the head including:
   a first carrier coupled to the head and operatively connected to a drive mechanism for moving the first carrier in a first path of motion, the first carrier having at least one of a plurality of bristles and an elastomeric cleaning member extending outwardly therefrom; and
   a resilient second carrier coupled to the head, the second carrier having at least one of a plurality of bristles and an elastomeric cleaning member extending outwardly from an upper surface of the second carrier, the second carrier having a longitudinal or transverse groove formed as a part thereof that permits the upper surface thereof to at least partially deform upon a force being applied to the upper surface such that the second carrier moves in a second path of motion different from the first path of motion.

13. The powered toothbrush of claim 12, further comprising a cavity defined in the second carrier.

14. The powered toothbrush of claim 12, wherein one end of the second carrier is shaped to conform to a peripheral edge of the first carrier.

15. The powered toothbrush of claim 12, wherein the elastomeric cleaning member of the second carrier comprises an upstanding elastomeric wall having a shape selected from the group consisting of linear, zigzag, and serpentine.

16. The powered toothbrush of claim 12, wherein the elastomeric cleaning member of the second carrier comprises a plurality of elastomeric fingers.

17. The powered toothbrush of claim 12, wherein the longitudinal or transverse groove is disposed in the upper surface of the second carrier.

18. A brush section for use in a powered toothbrush including a handle portion having a neck formed at one end, the brush section comprising:
a head adapted to be coupled to the neck, the head including:
a first carrier coupled to the head and operatively connected to a drive mechanism for moving the first carrier in a first path of motion, the first carrier having at least one of a plurality of bristles and an elastomeric cleaning member extending outwardly therefrom; and
a second carrier coupled to the head, the second carrier being formed of an elastomeric material and having at least one of a plurality of bristles and an elastomeric cleaning member extending outwardly from an upper surface of the second carrier, the upper surface of the second carrier having a weakened section comprising a longitudinal or transverse groove such that upon application of a force to the upper surface thereof, the upper surface at least partially collapses in a second path of motion resulting in movement of the at least one of a plurality of bristles and the elastomeric cleaning member, and upon removal of the force, the second carrier substantially returns to a non-collapsed condition.

19. The brush section of claim 18, wherein the second carrier defines a collapsible cavity formed between the upper surface and a lower surface thereof.

20. The brush section of claim 19, wherein the upper surface is collapsible to contact the lower surface upon application of the force.

* * * * *